United States Patent [19]

Schnell

[11] Patent Number: 5,569,298
[45] Date of Patent: Oct. 29, 1996

[54] RESPOSABLE SCISSORS

[76] Inventor: William J. Schnell, 1100 Crane Blvd., Libertyville, Ill. 60048

[21] Appl. No.: 236,991

[22] Filed: May 2, 1994

[51] Int. Cl.⁶ .................................................. A61B 17/00
[52] U.S. Cl. .......................................... 606/205; 606/174
[58] Field of Search ............................ 606/51, 52, 174, 606/205–211, 170; 128/751–755; 604/22

[56] References Cited

U.S. PATENT DOCUMENTS

| | | |
|---|---|---|
| 2,790,437 | 4/1957 | Moore . |
| 3,513,719 | 5/1970 | Tschanz . |
| 3,593,594 | 7/1971 | Perry . |
| 4,120,302 | 10/1978 | Ziegler . |
| 4,122,856 | 10/1978 | Moslor et al. . |
| 4,281,252 | 7/1981 | Parsons, Jr. et al. . |
| 4,407,167 | 10/1983 | Koukal et al. . |
| 4,569,131 | 2/1986 | Falk et al. . |
| 4,646,751 | 3/1987 | Maslanka . |
| 4,674,501 | 6/1987 | Greenberg . |
| 4,763,668 | 8/1988 | Macek et al. . |
| 4,869,351 | 9/1989 | Romano . |
| 4,977,900 | 12/1990 | Fehling et al. . |
| 4,986,825 | 1/1991 | Bays et al. . |
| 5,052,402 | 10/1991 | Bencini et al. . |
| 5,147,378 | 9/1992 | Markham . |
| 5,156,633 | 10/1992 | Smith . |
| 5,171,256 | 12/1992 | Smith et al. . |
| 5,171,258 | 12/1992 | Bales et al. . |
| 5,172,700 | 12/1992 | Bencini et al. . |
| 5,174,300 | 12/1992 | Bales et al. . |
| 5,192,298 | 3/1993 | Smith et al. . |
| 5,201,752 | 4/1993 | Brown et al. . |
| 5,203,785 | 4/1993 | Slater . |
| 5,209,755 | 5/1993 | Abrahan et al. . |
| 5,211,655 | 8/1993 | Hasson . |
| 5,215,101 | 6/1993 | Jacobs et al. . |
| 5,219,354 | 4/1993 | Choudhury et al. . |
| 5,219,357 | 6/1993 | Honkanen et al. . |
| 5,222,973 | 6/1993 | Sharpe et al. . |
| 5,234,460 | 8/1993 | Stouder, Jr. . |
| 5,241,968 | 9/1993 | Slater . |
| 5,251,638 | 10/1993 | Cottone, Jr. et al. . |
| 5,258,004 | 11/1993 | Bales et al. . |
| 5,275,607 | 1/1994 | Lo et al. . |
| 5,275,612 | 1/1994 | Bales, Jr. . |
| 5,282,800 | 2/1994 | Foshee et al. ............................ 606/52 |
| 5,290,308 | 3/1994 | Knight et al. ............................ 606/207 |
| 5,304,203 | 4/1994 | El-Mallawany ........................ 606/207 |
| 5,336,238 | 8/1994 | Holmes et al. ......................... 606/208 |
| 5,358,508 | 11/1994 | Cobb ....................................... 606/174 |
| 5,383,888 | 1/1995 | Zvenyatsky et al. ................... 606/205 |
| 5,391,166 | 2/1995 | Eggers ..................................... 606/174 |

FOREIGN PATENT DOCUMENTS

| | | |
|---|---|---|
| 0584787A1 | 8/1993 | European Pat. Off. . |
| 50053 | 9/1911 | Germany . |
| 2140735 | 12/1984 | United Kingdom . |

*Primary Examiner*—Stephen C. Pellegrino
*Assistant Examiner*—William W. Lewis
*Attorney, Agent, or Firm*—Kay H. P. Hannafan; Paul C. Flattery

[57] ABSTRACT

A surgical instrument has a hollow elongated shaft for insertion into the body, the shaft having a longitudinal axis and supporting a pair of interacting pivotable jaws on its distal end and being connected at its proximal end to a first movable component of an operating handle, with a reciprocable rod located within the shaft. The rod is connected to a second movable component of the handle for reciprocation within the shaft when the first and second components are moved relative to each other. The jaws are pivotally connected by a pivot pin supported on the shaft transversely to the axis. Each of the jaws has a proximal end extending proximally from the pivot pin. Each of the proximal ends is provided with an elongated opening therethrough, each the openings forming an elongated slot oriented at an oblique angle relative to the longitudinal axis of the shaft. The reciprocable rod has a distal end extending into each slot whereby reciprocation of the rod causes the jaws to open and close.

6 Claims, 3 Drawing Sheets

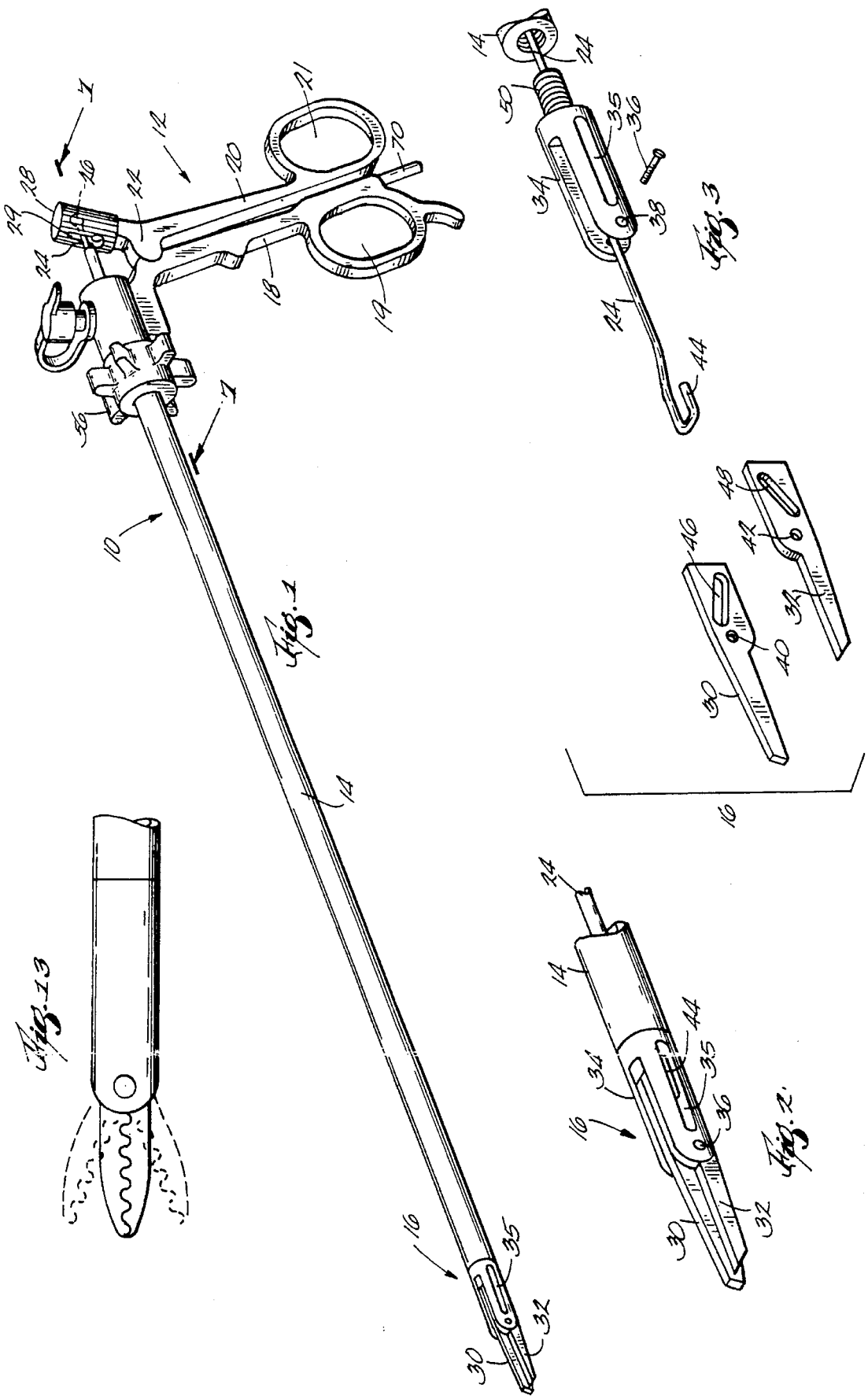

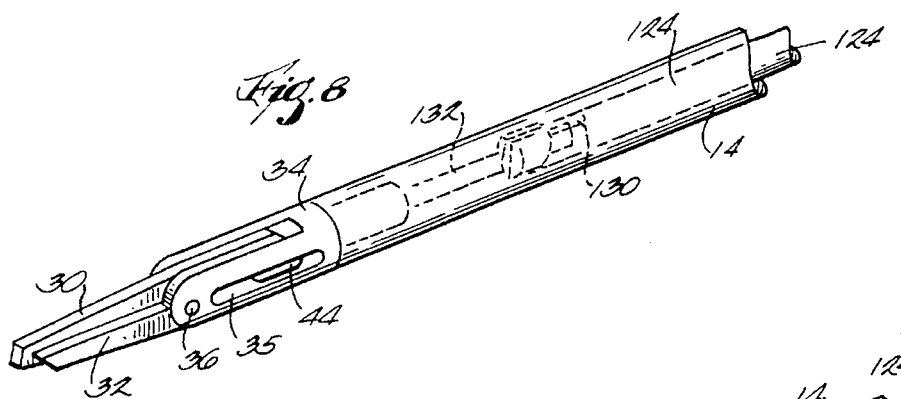
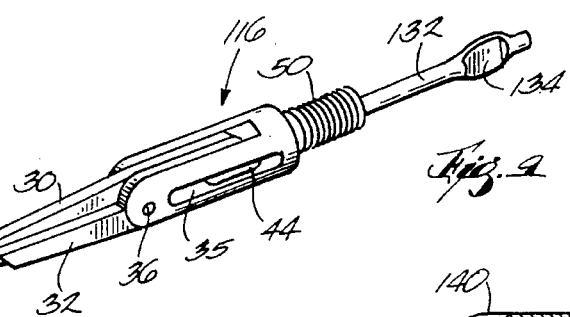
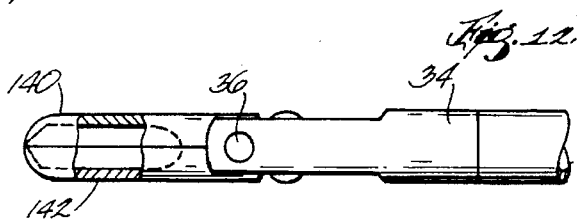
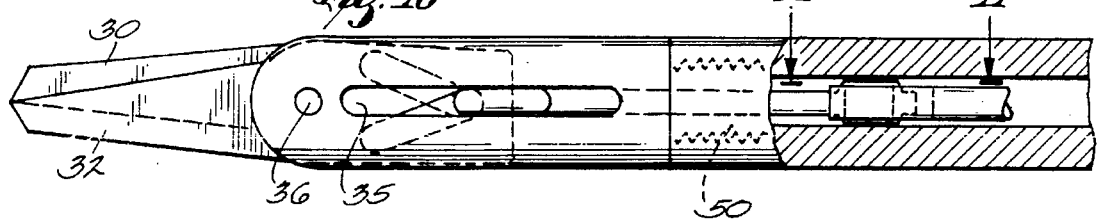
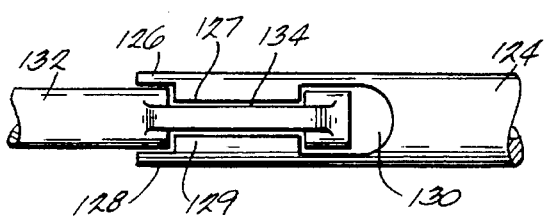

5,569,298

RESPOSABLE SCISSORS

FIELD OF THE INVENTION

The present invention relates to surgical instruments such as laparoscopic scissors, dissectors or grasping jaws.

BACKGROUND OF THE INVENTION

Laparoscopic procedures generally involve excising or manipulating tissue through an opening in the body typically through a cannula through which a pivoting jaw type surgical instrument is inserted. Various mechanisms have heretofore been proposed for actuation of the jaws of such devices. Examples are U.S. Pat. Nos. 2,790,437; 5,171,256; 5,171,258; 5,172,700 and 5,192,298. Typically the instrument, including handle, shaft and working tip are all reusable. However, particularly in the case of scissors, the delicate blades dull or are easily damaged. Thus it is desirable and cost efficient to be able to replace just the working tip components of the instrument.

The prior art instruments have tended to either have one stationary jaw and one pivotal jaw or to use an actuating mechanism, for causing pivoting of both jaws, that has a significant number of working parts. A need has, thus, existed for an instrument wherein a simplified mechanism is provided for causing pivoting of jaws or blades.

SUMMARY OF THE INVENTION

A major object of the present invention is to provide a surgical instrument of the endoscopic type having a simplified mechanism for reciprocating a pair of jaws or blades. In accordance with one aspect of the invention, a pair of jaws, which may be in the form of dissectors, graspers or scissors, are both pivotally supported on the distal end of the instrument and are operated to open and close utilizing a minimum number of working parts. More specifically, it is an important aspect of the invention to operate a pair of jaws or blades about a pivot point that supports the jaws on the distal end of an endoscopic instrument tube or hollow shaft with pivoting about the pivot point being caused by reciprocation of a central rod reciprocal within the shaft. In accordance with a related object, the distal end of the reciprocal rod is slidably positioned in a pair of slots, one of which is provided in the proximal end of each of the jaws.

In accordance with a still further aspect of the invention, a pair of jaws is provided with slots in the proximal end thereof which slots are positioned at an oblique angle relative to the longitudinal axis of the main shaft of the instrument.

Briefly summarized, the invention provides a surgical instrument which has a hollow elongated shaft for insertion into the body. The shaft has a longitudinal axis and supports a pair of interacting pivotable jaws on its distal end and is connected at its proximal end to a first movable component of an operating handle, with a reciprocable rod located within the shaft. The rod is connected to a second movable component of the handle for reciprocation within the shaft when the first and second components are moved relative to each other. The jaws are pivotally connected by a pivot pin supported transversely to the axis of the shaft. Each of the jaws has a proximal end extending proximally from the pivot pin. Each of the proximal ends is provided with an elongated opening therethrough, each the openings forms an elongated slot oriented at an oblique angle relative to the longitudinal axis of the shaft. The reciprocable rod has a distal end extending into each slot whereby reciprocation of the rod causes the jaws to open and close.

Further objects and advantages of the invention will be apparent from the following detailed description, accompanying drawings and appended claims.

BRIEF DESCRIPTION OF THE DRAWINGS

FIG. 1 is a perspective view of a surgical instrument in accordance with the invention;

FIG. 2 is an enlarged perspective fragmentary view of the distal tip portion of the instrument of FIG. 1;

FIG. 3 is an exploded perspective view of the fragmentary portion of FIG. 2 shown in an exploded position to illustrate the specific details of the pivotal jaws of the instrument;

FIG. 8 is an enlarged fragmentary perspective view of an alternative embodiment of the invention with interior parts shown by phantom lines;

FIG. 9 is an exploded view of the interior reciprocal rod and distal tip component of the embodiment shown in FIG. 8;

FIG. 10 is an enlarged side elevational view of the distal tip portion of the embodiment of FIG. 8 with interior parts shown by phantom lines and with some parts shown in cross-section for clarity of the working mechanism; and FIG. 11 is a top plan view of the device of FIG. 10 taken along line 11—11;

FIG. 12 is an alternate form of the end cutting instrument;

FIG. 13 is another alternate form of the end cutting instrument.

DETAILED DESCRIPTION OF PREFERRED EMBODIMENTS

Figure 4:
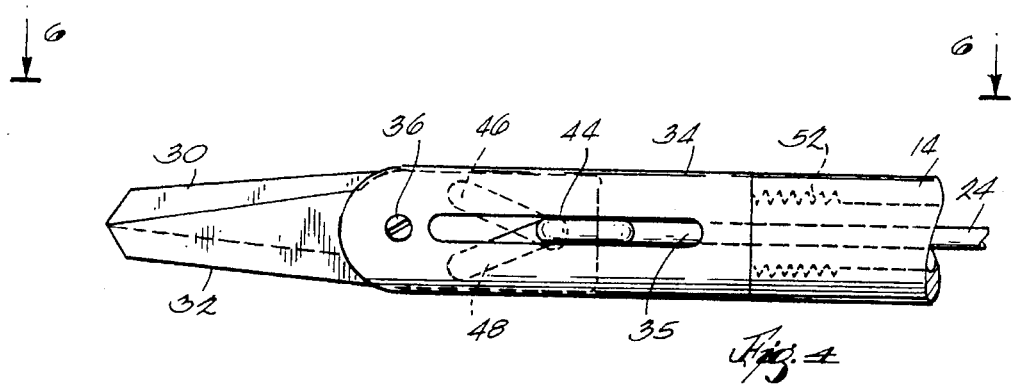
FIG. 4 is an enlarged fragmentary side elevational view of the distal tip of the instrument of FIG. 1 with interior parts illustrated by phantom lines.

Referring more specifically to the drawings, a surgical instrument 10 is provided with a handle portion generally designated by numeral 12 to which is attached a hollow shaft 14 which supports a reciprocal jaw distal end tool 16. Handle component 12 includes pivotally connected components 18 and 20 provided with finger openings 19 and 21, respectively. The components 18 and 20 are pivotally connected at a point 22 for movement relative to each other. A central rod 24 is movably positioned within the interior of hollow shaft 14. Rod 24 is provided with an enlarged end 26 which is connected to a cap 28 carried at the top of pivotal handle section 20. Cap 28 is slidable upwardly and downwardly and contains a keyhole shaped opening 29 adapted to retain the enlarged end 26 when it is in the down position illustrated in FIG. 1 but which allows removal of rod 24 when cap 28 is raised to enable enlarged end 26 to slide Out of the enlarged end of opening 29.

End tool 16 includes reciprocable scissors blades 30 and 32 which are pivotally attached to the distal end component 34 of the instrument. As best seen in FIGS. 2 and 3, the blades are pivotally connected by means of a pivot pin 36 to a bifurcated distal end of tip component 34 which also is provided with slots 35 on its lateral edges. Tip component 34 is provided with openings 38 to receive pivot pin 36. Similarly, the blades 30 and 32 are provided with openings 40 and 42 to receive the pivot pin 36. Distal end component 34 is provided with a threaded shaft 50 which is received by mating threads 52 in the distal end of hollow shaft 14.

As best seen in FIG. 3, the distal end 44 of central rod 24 is bent into a hook configuration, so that a section thereof is oriented transversely to the longitudinal axis of rod 24. The distal end portion 44 is adapted to be slidably received in lateral slots 35 of distal end component 34. The distal end 44 is also slidably received in slots 46 and 48, which are located in the proximal ends of blades 30 and 32. As best seen in FIG. 3 slots 46 and 48 are located in the blades at an oblique angle relative to the longitudinal axis of the blades. The slots extend from a distal end adjacent the outer lateral side of each blade and extend in a proximal direction at an angle inclined toward the inner, or cutting surface sides of the respective blades 30 and 32. Thus, as the distal end 44 of rod 24 is reciprocated within hollow shaft 14 it slides within each of the slots 46 and 48 thereby causing the blades 30 and 32 to be reciprocated about pivot pin 36. The blades therefore are caused to open and close as the handle components 18 and 20 are opened and closed.

Figure 5:
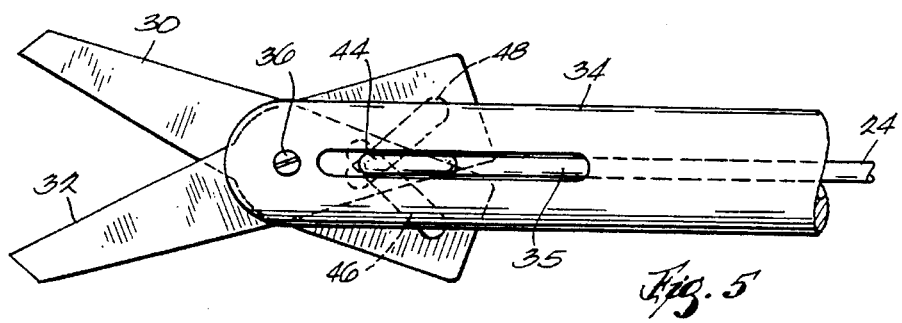
FIG. 5 is an enlarged fragmentary view of the distal tip shown in FIG. 4 with the jaws pivoted to the open position.
Figure 6:
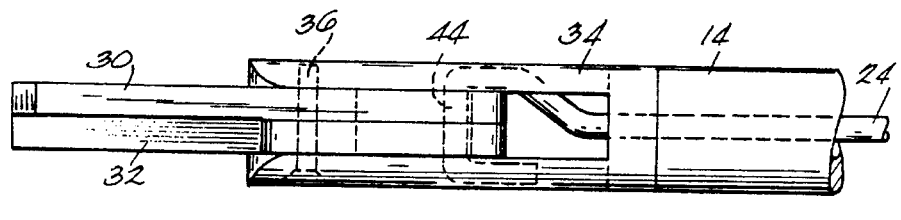
FIG. 6 is a top plan view of the distal tip shown in FIG. 4 taken along lines 6—6.

The closed position of the blades 30, 32 is seen in FIG. 4, while the open position thereof is best seen in FIG. 5.

Figure 7:
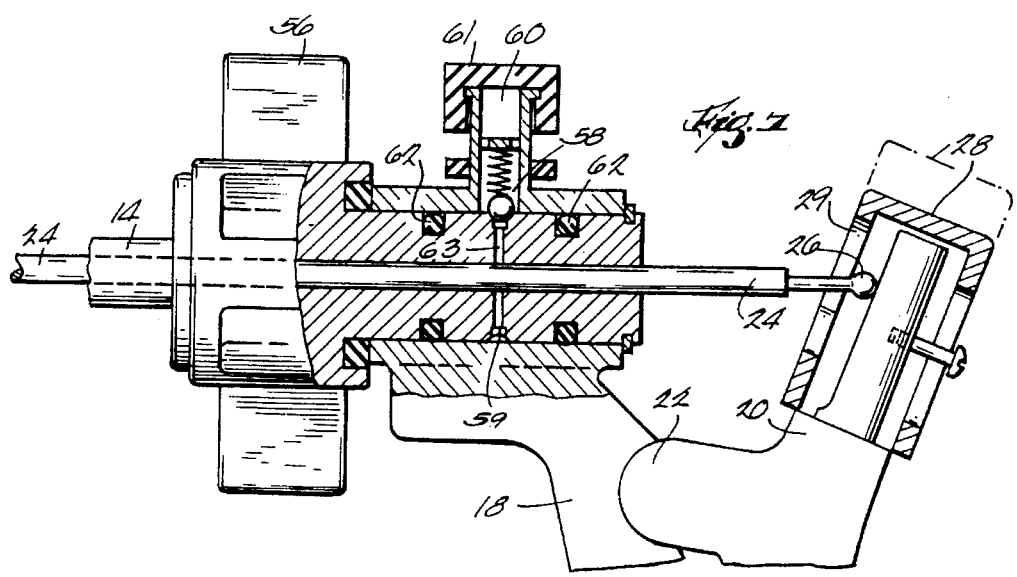
FIG. 7 is a fragmentary side view of the handle working mechanism and proximal end of the reciprocal rod and hollow shaft of the device shown in FIG. 1 taken along line 7—7 with parts in cross-section to show interior details.

As seen in FIG. 7, a fluid inlet tube 60 communicates with the inside of tubular shaft 14. Orifice 60 can be closed by means of a cap, for example, of the snap-on plastic type 61. A spring biased detente ball 58 can be utilized to retain the rotational orientation of shaft 14 in a desired relationship. Handles 56 are attached to the exterior of shaft 14 to enable easy rotation thereof. Indentions 59 in the outer surface of shaft 14 receive detente ball 58.

Seals 62 of the rubber O-ring type prevent fluid escape along the outside of shaft 14. Orifices 63 are provided to allow fluid communication to the interior of shaft 14. Thus, a means of introducing cleaning fluid to the interior of the reciprocal members 14, 24 is provided.

As seen in FIG. 1, an electrode 70 can be provided extending downwardly from scissors handle 18. Electrode 70 is adapted to receive electrical power for transmission to metal tube 14 and thence to the end effectors 30, 32 for use in cauterization procedures.

In the modified version of the invention shown in FIGS. 8–11, central reciprocable rod 24 is replaced with a two piece rod 124, 132. In the case of this embodiment, only tip assembly 116 is discarded. The proximal portion of the rod 124 remains as a permanent part of the handle assembly. As best seen in FIGS. 8 and 9, the distal end of rod 124 is divided into bifurcations 126 and 128. These bifurcations have inwardly extending projections 127 and 129. Enlarged opening 130 is located proximally to the projections 127 and 129. The disposable distal tip assembly that carries the scissors blades 30 and 32 and the related working parts substantially the same as those described relative to FIGS. 1–7 is best seen in FIG. 9. A shaft 132 is provided with a working end 44. Shaft 132 is provided with an indented portion 134 preferably formed by swaging an appropriate indentation on each side of the shaft. Indentations 134 are appropriately sized to be engaged by projections 127 and 129 to hold the assembly together in the retracted position illustrated in FIG. 8. The shafts 124 and 132 are therein shown in the connected position withdrawn into the hollow lumen of shaft 114.

In addition to a scissors 30, 32, the end cutting instrument can take different forms. For example, in FIG. 12, the end tool includes jaws 140 and 142 shaped to be used as a biopsy instrument. In the embodiment of FIG. 13, jaws are provided with serrated mating jaw surfaces desirable in some dissection or grasping procedures. It will be apparent to those skilled in the art that still further forms of mating jaw surfaces can be actuated by the mechanism of the present invention.

It is, thus, seen that the invention has produced a novel and superior working mechanism for a surgical instrument utilizing working jaws. Those novel features are set forth with particularity in the appended claims.

What is claimed is:

1. A surgical instrument comprising:

a hollow elongated shaft for insertion into the body, said shaft having a distal end supporting a tip component, said shaft being connected at its proximal end to a first movable component of an operating handle, said distal tip component having a longitudinal axis and a bifurcated distal end supporting a pair of interacting pivotable jaws, said distal tip component also having a pair of slots on its lateral edges, said jaws being pivotally connected by a pivot pin supported transversely to the axis of said tip component each of said jaws having a proximal end extending proximally from said pivot pin, each of said proximal ends being provided with an elongated opening therethrough, each of said openings forming an elongated slot oriented at an oblique angle relative to said longitudinal axis, and a reciprocal rod being located within said shaft, a proximal end of said rod being connected to a second movable component of said handle for reciprocation within said shaft when said first and second components are moved relative to each other, said reciprocal rod having a distal end bent in a hook configuration having a section thereof oriented transversely to the longitudinal axis of said rod, said section extending into each of said elongated slots and the elongated openings of said jaws, whereby reciprocation of said rod causes said jaws to open and close.

2. An instrument according to claim 1 wherein said jaws comprise scissors blades.

3. An instrument according to claim 1 wherein said reciprocal rod is of one piece and extends through the entire length of said hollow elongated shaft.

4. An instrument according to claim 1 wherein said reciprocal rod is of two parts comprising a distal segment and a proximal segment, said distal and proximal segments being connected to each other within said shaft.

5. An instrument according to claim 4 wherein the distal end of the proximal segment of said rod is bifurcated and said bifurcations have inwardly extending projections, the proximal end of said distal portion having mating notches on the opposite sides thereof for engagement by said projections.

6. An instrument according to claim 1 wherein each of said elongated slots in each of said jaws extends from a distal end located relatively closer to a lateral edge of said jaw and extends to a proximal end located closer to a cutting edge of said jaw.

\* \* \* \* \*